US006537992B2

(12) United States Patent
Parker

(10) Patent No.: US 6,537,992 B2
(45) Date of Patent: Mar. 25, 2003

(54) REGULATION OF ORGANIC NITRATE TOLERANCE

(75) Inventor: John D. Parker, 15 Oakly Place, Toronto, Ontario (CA), M2P 2G3

(73) Assignee: John D. Parker (CA)

( * ) Notice: Subject to any disclaimer, the term of this patent is extended or adjusted under 35 U.S.C. 154(b) by 0 days.

(21) Appl. No.: 09/754,196

(22) Filed: Jan. 5, 2001

(65) Prior Publication Data

US 2002/0091126 A1 Jul. 11, 2002

(51) Int. Cl.$^7$ ............................................. A61K 31/495
(52) U.S. Cl. ........................................................ 514/249
(58) Field of Search ......................................... 514/252

(56) References Cited

U.S. PATENT DOCUMENTS

| | | | | |
|---|---|---|---|---|
| 5,922,713 A | * | 7/1999 | Warner ........................ | 514/249 |
| 5,945,452 A | * | 8/1999 | Cooke et al. ................ | 514/564 |
| 6,117,872 A | * | 9/2000 | Maxwell et al. ............. | 514/252 |
| 6,127,370 A | * | 10/2000 | Smith et al. ................. | 514/252 |
| 2002/0052374 A1 | | 5/2002 | Rabelink et al. ............ | 514/250 |

FOREIGN PATENT DOCUMENTS

| | | | | |
|---|---|---|---|---|
| DE | 199 20 775 | | 11/2000 | .......... A61K/45/00 |

OTHER PUBLICATIONS

Adak et al, J. Biological Chem., vol. 275, No. 43, pp. 33554–33561 (Oct. 2000).*
Bune et al, Biochemical & Biophysical Res. Comm., vol. 220, pp. 13–19 (1996).*
Seiji Ueda, et al., "Tetrahydrobiopterin Restores Endothelial Function in Long–Term Smokers", J. of the American College of Cardiology, vol. 35, No. 1, Jan., 2000, pp. 71–75.
Hanneke W. Wilmink, et al., "Influence of Folic Acid on Postprandial Endothelial Dysfunction", Arterioscler. Thromb. Vasc. Biol., vol. 20, Jan., 2000, pp. 185–188.
Stephen D. Milone, et al., "Biochemical, Hemodynamic, and Vascular Evidence Concerning the Free Radical Hypothesis of Nitrate Tolerance", J. of Cardiovascular Pharmacology, vol. 33, No. 5, (1999) pp. 685–690.
Sabine Kurz, et al., "Evidence for Casual Role of the Renin–Angiotensin System in Nitrate Tolerance", Circulation, vol. 99, (1999) pp. 3181–3187.
John D. Parker, et al., "Nitrate Therapy for Stable Angina Pectoris", The New Eng. J. of Med., vol. 338, No. 8, Feb. 19, 1998, pp. 520–531.
Marianne C. Verhaar, et al., "5–Methyltetrahydrofolate, the Active Form of Folic Acid, Restores Endothelial Function in Familial Hypercholesterolemia", Circulation, vol. 97, (1998) pp. 237–241.

Erik Stroes, et al., "Tetrahydrobiopterin Restores Endothelial Function in Hypercholesterolemia", J. Clin. Invest., vol. 99, No. 1, Jan., 1997, pp. 41–46.
Jørn Bech Laursen, et al., "Nitrate Tolerance Impairs Nitric Oxide–Mediated Vasodilation in Vivo", Cardiovascular Research, vol. 31, (1996) pp. 814–819.
Chao Han, et al., "Pharmacokinetics of Nitroglycerin and Its Four Metabolites During Nitroglycerin Transdermal Administration", Biopharmaceutics & Drug Disposition, vol. 15, (1994) pp. 179–183.
Georgette M. Buga, et al., "Negative Feedback Regulation of Endothelial Cell Function by Nitric Oxide", Circulation Research, vol. 73, No. 5, Nov., 1993, pp. 808–812.
Frank W. Lee, et al., "Pharmacokinetics and Pharmacodynamics of Nitroglycerin and Its Dinitrate Metabolites in Conscious Dogs: Intravenous Infusion Studies", J. of Pharm. and Biopharm., vol. 21, No. 5, (1993) pp. 533–550.
Walter E. Haefeli, et al., "Comparison of Vasodilatory Responses to Nitroglycerin and its Dinitrate Metabolites in Human Veins", Clin. Pharmacol. Ther., vol. 52, No. 6, Dec., 1992, pp. 590–596.
M. Gumbleton, et al., "Pharmacological Activity of the Dinitrate Metabolites of Nitroglycerin Following their Oral Administration to Healthy Volunteers", Br. J. Clin. Pharmacol., vol. 31, (1991) pp. 211–213.
Dale K. Yu, et al., "Pharmacokinetics of Nitroglycerin and Metabolites in Humans Following Oral Dosing", Biopharmaceutics & Drug Disposition, vol. 9, (1988) pp. 557–565.
B. Mayer, et al.: "Biosynthesis and action of nitric acid oxide in mammalian cells", TIBS 22—Dec. 1997, pp. 477–481.
E. Stroes, et al.: "Origin of superoxide production by endothelial nitric oxide synthase", FEBS Letters 438 (1998), pp. 161–164.
Database Biosis Online!, Biosciences Information Service, W. Kaesemeyer, et al., Endothelial nitric oxide synthase is a site of superoxide synthesis in endothelial cells treated wit glyceryl trinitrate.
R.M.F. Weaver, et al.: "Tetrahydrobiopterin regulates superoxide and nitric oxide generation by recombinant endothelial nitric oxide synthase", Biochemical And Biophysical Research Communications 237 (1997), pp. 340–344.

* cited by examiner

*Primary Examiner*—James H. Reamer
(74) *Attorney, Agent, or Firm*—Katten Muchin Zavis Rosenman

(57) ABSTRACT

There is disclosed pharmaceutical compositions and methods useful in obviating or mitigating tolerance during organic nitrate therapy. The compositions and methods comprise compounds selected from the group comprising a folate compound, a folate derivative compound, tetrahydrobiopterin and mixtures thereof.

20 Claims, No Drawings

REGULATION OF ORGANIC NITRATE TOLERANCE

BACKGROUND OF THE INVENTION

1. Field of the Invention

In one of its aspects, the present invention relates to a pharmaceutical composition for regulation of organic nitrate tolerance. In another of its aspects, the present invention relates to a method for regulating organic nitrate tolerance.

2. Description of the Prior Art

Organic nitrates such as glyceryl trinitrate, isosorbide dinitrate, isosorbide-5-mononitrate, and the like are recognized as important pharmacologic agents used in the treatment of coronary artery disease and congestive heart failure—see Parker J. Nitrate Therapy for Stable Angina Pectoris. *N Engl J Med.* 1998;338:520–531. Despite successful application, the use of nitroglycerin is limited by a number of its pharmacologic characteristics. One of the important limitations is loss of efficacy during continuous therapy, a phenomenon known as "tolerance". The etiology of tolerance is not clearly understood, however recent experimental data have improved the understanding of the mechanism(s) involved—see one or more of:

a. Münzel T, Sayegh H, Freeman B A et al. Evidence for enhanced vascular superoxide anion production in nitrate tolerance. A novel mechanism underlying tolerance and cross-tolerance. J Clin Invest 1995; 95 (1):187–94;

b. Münzel T, Li H, Mollnau H, Hink U et al. Effects of long-term nitroglycerin treatment on endothelial nitric oxide synthase (NOS III) gene expression, NOS III-mediated superoxide production, and vascular NO bioavailability. Circ Res 2000; 86 (1): E7–E12; and c. Münzel T, Mollnau H, Hartmann M et al. Effects of a nitrate-free interval on tolerance, vasoconstrictor sensitivity and vascular superoxide production. J Am Coll Cardiol 2000; 36 (2): 628–34.

Thus it would desirable to have a pharmaceutical composition which obviates or mitigates tolerance to organic nitrate therapy.

SUMMARY OF THE INVENTION

It is an object of the present invention to provide a novel composition which is useful to obviate or mitigate tolerance to organic nitrate therapy.

It is another object of the present invention to provide a novel method for regulating tolerance to organic nitrate therapy.

Accordingly, in one of its aspects, the present invention provides an organic nitrate therapy tolerance regulation pharmaceutical composition comprising a folate compound, a folate derivative compound, tetrahydrobiopterin and mixtures thereof, together with a pharmaceutically acceptable carrier therefor.

In another of its aspects, the present invention provides a method for regulating tolerance during organic therapy, the method comprising the step of administering to a patient undergoing organic nitrate therapy a pharmaceutical composition comprising a folate compound, a folate derivative compound, tetrahydrobiopterin and mixtures thereof, together with a pharmaceutically acceptable carrier therefor.

In yet another of its aspects, the present invention provides a pharmaceutical composition comprising:

(i) a first active ingredient comprising an organic nitrate;

(ii) a second active ingredient comprising a folate compound, a folate derivative compound, tetrahydrobiopterin and mixtures thereof; and (iii) a pharmaceutically acceptable carrier therefor.

In yet another of its aspects, the present invention provides a kit for use in organic nitrate therapy, the kit comprising:

(i) a first pharmaceutical composition comprising an organic nitrate, together a pharmaceutically acceptable carrier therefor;

(ii) a second pharmaceutical composition comprising a folate compound, a folate derivative compound, tetrahydrobiopterin and mixtures thereof, together with a pharmaceutically acceptable carrier therefor.

In yet another of its aspects, the present invention provides a method for regulating tolerance during organic nitrate therapy, the method comprising the step of administering to a patient:

(i) a first pharmaceutical composition comprising an organic nitrate, together a pharmaceutically acceptable carrier therefor; and (ii) a second pharmaceutical composition comprising a folate compound, a folate derivative compound, tetrahydrobiopterin and mixtures thereof, together with a pharmaceutically acceptable carrier therefor.

In yet another of its aspects, the present invention provides for the use of a compound selected from the group comprising a folate compound, a folate derivative compound, tetrahydrobiopterin and mixtures thereof for the production of a pharmaceutical composition useful in regulated tolerance to organic nitrate therapy.

DETAILED DESCRIPTION OF THE PREFERRED EMBODIMENTS

Thus, I have surprisingly and unexpectedly discovered that selected compounds are useful in obviating or mitigating tolerance during organic nitrate therapy.

The compounds may be selected from the group comprising a folate compound, a folate derivative compound, tetrahydrobiopterin and mixtures thereof. The term "folate derivative compound" will be readily understood by those of skill in the art to encompass compounds having a folate "backbone" which has been derivatized. Non-limiting examples of suitable such compounds may be selected from the group comprising tetrahydrofolate, 5-methyltetrahydrofolate and mixtures thereof.

The dosage administered of the folate compound, the folate derivative compound or the tetrahydrobiopterin will vary depending on the use and known factors such as the pharmacodynamic characteristics of the particular substance, and its mode and route of administration; age, health, and weight of the individual recipient; nature and extent of symptoms, kind of concurrent treatment, frequency of treatment, and the effect desired.

For use in co-administration with and organic nitrate for the treatment of coronary artery disease and/or congestive heart failure, by way of general guidance, a daily dosage of an active ingredient such as the folate compound, the folate derivative compound or the tetrahydrobiopterin can be in the range of from about 0.01 to about 80 mg/kg of body weight, preferably from about 0.1 to about 20, more preferably from about 0.2 to about 10 mg/kg of body weight. Ordinarily a dose of from about 0.5 to about 50 mg/kg per day of the folate compound, the folate derivative compound or the tetrahydropterin in divided doses one to multiple times a day, preferably up to four times per day, or in sustained release form is effective to obtain the desired results.

In the treatment methods and compositions of the present invention, the folate compound, the folate derivative compound or the tetrahydrobiopterin described in detail herein is (are) the active ingredient(s), and are typically administered for oral, topical, rectal, parenteral, local, inhalant or intracerebral use. In an embodiment of the invention, the substances are administered in intranasal form via topical use of suitable intranasal vehicles, or via transdermal routes, using forms of transdermal skin patches known to those of ordinary skill in that art. To be administered in the form of a transdermal delivery system, the dosage administration will be continuous rather than intermittent throughout the dosage regimen. The substances can also be administered by way of controlled or slow release capsule system and other drug delivery technologies.

A preferred form of administration is oral. For example, for oral administration in the form of a tablet or capsule, the active substance(s) can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and colouring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcelluose, polyethylene glycol, waxes, and the like. Suitable lubricants used in these dosage forms include sodium oleate, sodium stearate, magnesium stearate, sodium benxoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain colouring and flavouring agents to increase patient acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfate, or ascrobic acid, either alone or combined, citric acid and its salts and sodium EDTA. Parenteral solutions may also contain preservatives, such as benzalkonium chloride, methyl- or propyl-paraben, and chlorobutanol.

The active ingredient substances described in detail herein can also be administered in the form of liposome delivery system, such as small unilamellar vesicles, large unilamellar vesicles, and multilamellar vesicles. Liposomes can be formed from a variety of phospholipids, such as cholesterol, stearylamine, or phosphatidylcholines.

The active ingredient substances described in detail herein may also be coupled with soluble polymers which are targetable drug carriers. Examples of such polymers include polyvinylpyrrolidone, pyran copolymer, polyhydroxypropylmethacrylamide-phenol, polyhydroxyethyl-aspartamidephenol, or polyethyleneoxide-polylysine substituted with palmitoyl residues. The active ingredient substances may also be coupled to biodegradable polymers useful in achieving controlled release of a drug. Suitable polymers include polyactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. The substances can also be affixed to rigid polymers and other structures such as fullerenes or Buckeyballs.

Pharmaceutical compositions suitable for administration contain about 1 milligram to 1500 milligrams of active substance per unit. In these pharmaceutical compositions, the active ingredient will ordinarily be present in an amount of about 0.5–95% by weighty based on the total weight of the composition.

Suitable pharmaceutical carriers and methods of preparing pharmaceutical dosage forms are described in Remington's Pharmaceutical Sciences, Mack Publishing Company, a standard reference text in this field.

As will be developed hereinbelow, it has been surprisingly and unexpectedly discovered that supplemental oral folate is effective in minimizing or preventing the development of tolerance to the vascular effects of nitroglycerin.

Normal volunteers (n=20) were randomized in a double bind, placebo-controlled fashion to either oral folate (5 mg per day) or placebo. After 1 week of this double-blind therapy, subjects returned to the laboratory. At that time, measures of standing systolic blood pressure and heart rate were recorded. Subsequently, measurements of forearm blood flow were made at rest and in response to sublingual nitroglycerin (0.6 mg). Forearm blood flow was measured using strain gauge plethysmography as described in Milone et al., The Angiotensin II Receptor Antagonist Losartan Does Not Prevent Tolerance to Nitroglycerin. A Randomized Double-blind, Placebo-controlled Study, *J Cardiovasc Pharm.* 1999;34:645–659.

Subsequently all subjects all received transdermal GTN (0.6 mg/hr). Standing heart rate and blood pressure responses were repeated 3 hours after initial patch application. Subjects were discharged from the laboratory with instructions to take transdermal GTN continuously for the next 5 to 7 days, changing the patch each day at 0800 hours. After 5 to 7 days, subjects returned to the laboratory where measures of standing systolic blood pressure and heart rate as well as forearm blood flow were repeated.

In both the placebo and folate therapy group, the acute administration of transdermal GTN caused a significant fall in systolic blood pressure as well as a significant increase in heart rate. The administration of subligual GTN also caused a similar, significant increase in forearm blood flow in both groups. When subjects returned, 5 to 7 days later, standing systolic blood pressure had returned to baseline values in the placebo group and their forearm blood flow response to subligual GTN was markedly blunted. Both of these hemodynamic observations indicate the development of tolerance to GTN in the placebo group. In contrast, in the folate group, standing systolic blood pressure remained significantly decreased as compared to baseline values following 5 to 7 days of transdermal GTN therapy. Further, their forearm blood flow responses to sublingual GTN remained unchanged as compared to responses prior to GTN therapy. These findings demonstrate that supplemental folate therapy prevents the development of tolerance during continuous therapy with GTN.

These findings provide evidence that tolerance to organic nitrates is caused by abnormalities in the function of NOS (nitric oxide synthase). While not wishing to be bound by any particular theory or mode of action, these abnormalities in the function of the enzyme appear to be caused by an uncoupling of the dimer, mediated by a reduction in tetrahydrobiopterin (BH4). Therefore, tolerance can be obviated or mitigated by the co-administration of supplemental BH4, or, alternatively, by the administration of supplemental folate which facilitates the regeneration of BH4 from its oxidized form dihydrobiopterin (BH2).

While this invention has been disclosed with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. An organic nitrate therapy tolerance regulation pharmaceutical composition for administration to a patient receiving an organic nitrate, the composition comprising a member selected from the group consisting essentially of a folate compound, a folate derivative compound, tetrahydrobiopterin and mixtures thereof, together with a pharmaceutically acceptable carrier therefor.

2. The composition defined in claim 1, wherein the folate derivative compound is selected from the group comprising tetrahydrofolate, 5-methyltetrahydrofolate and mixtures thereof.

3. A method for regulating tolerance to organic nitrate therapy in a patient who is receiving an organic nitrate, the method comprising the step of administering to the patient a pharmaceutical composition comprising a member selected from the group consisting essentially of a folate compound, a folate derivative compound, tetrahydrobiopterin and mixtures thereof, together with a pharmaceutically acceptable carrier therefor.

4. The method defined in claim 3, wherein the folate derivative compound is selected from the group comprising tetrahydrofolate, 5-methyltetrahydrofolate and mixtures thereof.

5. A pharmaceutical composition for (i) administration to a patient to whom is being administered an organic nitrate, and (ii) regulation of tolerance to organic nitrate in the patient, the composition comprising:
   (i) a first active ingredient comprising an organic nitrate;
   (ii) a second active ingredient comprising a member selected from the group consisting essentially of a folate compound, a folate derivative compound, tetrahydrobiopterin and mixtures thereof; and
   (iii) a pharmaceutically acceptable carrier therefor.

6. The composition defined in claim 5, wherein the folate derivative compound is selected from the group comprising tetrahydrofolate, 5-methyltetrahydrofolate and mixtures thereof.

7. A kit for regulation of tolerance to organic nitrate therapy in a patient, the kit comprising:
   (i) a first pharmaceutical composition comprising an organic nitrate, together a pharmaceutically acceptable carrier therefor;
   (ii) a second pharmaceutical composition comprising a member selected from the group consisting essentially of a folate compound, a folate derivative compound, tetrahydrobiopterin and mixtures thereof, together with a pharmaceutically acceptable carrier therefor.

8. The kit defined in claim 7, wherein the folate derivative compound is selected from the group consisting tetrahydrofolate, 5-methyltetrahydrofolate and mixtures thereof.

9. A method for regulating tolerance to organic nitrate therapy in a patient who is receiving an organic nitrate, the method comprising the step of administering to a patient:
   (i) a first pharmaceutical composition comprising an organic nitrate, together a pharmaceutically acceptable carrier therefor; and
   (ii) a second pharmaceutical composition comprising a member selected from the group consisting essentially of a folate compound, a folate derivative compound, tetrahydrobiopterin and mixtures thereof, together with a pharmaceutically acceptable carrier therefor.

10. The method defined in claim 9, wherein the folate derivative compound is selected from the group comprising tetrahydrofolate, 5-methyltetrahydrofolate and mixtures thereof.

11. The composition defined in claim 1, wherein the organic nitrate therapy comprises treatment of coronary artery disease.

12. The composition defined in claim 1, wherein the organic nitrate therapy comprises treatment of congestive heart failure.

13. The method defined in claim 3, wherein the organic nitrate therapy comprises treatment of coronary artery disease.

14. The method defined in claim 3, wherein the organic nitrate therapy comprises treatment of congestive heart failure.

15. The composition defined in claim 5, wherein the organic nitrate therapy comprises treatment of coronary artery disease.

16. The composition defined in claim 5, wherein the organic nitrate therapy comprises treatment of congestive heart failure.

17. The kit defined in claim 7, wherein the organic nitrate therapy comprises treatment of coronary artery disease.

18. The kit defined in claim 7, wherein the organic nitrate therapy comprises treatment of congestive heart failure.

19. The method defined in claim 9, wherein the organic nitrate therapy comprises treatment of coronary artery disease.

20. The method defined in claim 9, wherein the organic nitrate therapy comprises treatment of congestive heart failure.

* * * * *